United States Patent [19]
Skelnik

[11] Patent Number: 6,153,582
[45] Date of Patent: Nov. 28, 2000

[54] DEFINED SERUMFREE MEDICAL SOLUTION FOR OPHTHALMOLOGY

[75] Inventor: Debra L. Skelnik, Cambridge, Minn.

[73] Assignee: Bausch & Lomb Surgical, Inc., St. Louis, Mo.

[21] Appl. No.: 09/186,580

[22] Filed: Nov. 5, 1998

[51] Int. Cl.[7] .......................... A61K 38/00; A61K 31/70
[52] U.S. Cl. ................... 514/12; 514/62; 514/912
[58] Field of Search .................... 514/12, 62, 912

[56] References Cited

U.S. PATENT DOCUMENTS 4,911,933  3/1990  Gilbard .................... 424/663

Primary Examiner—Zohreh Fay
Attorney, Agent, or Firm—Hugh D. Jaeger

[57] ABSTRACT

A defined serumfree medical solution for applications in Ophthalmology, that contains one or more cell nutrient supplements, and a growth factor(s) which maintains and enhances the preservation of eye tissues, including human corneal, retinal and corneal epithelial tissues at low to physiological temperatures (2° C. to 38° C.). This solution is composed of a defined aqueous nutrient and electrolyte solution, supplemented with a glycosaminoglycan(s), a deturgescent agent(s), an energy source(s), a buffer system (s), an antioxidant(s), membrane stabilizing agents, an antibiotic(s) and/or antimycotic agent(s), ATP or energy precursors, nutrient cell supplements, coenzymes and enzyme supplements, nucleotide precursors, hormonal supplements, non-essential amino acids, trace minerals, trace elements and a growth factor(s).

41 Claims, 1 Drawing Sheet

FIG. 1

DEFINED SERUMFREE MEDICAL SOLUTION FOR OPHTHALMOLOGY

CROSS REFERENCES TO CO-PENDING APPLICATIONS

None.

BACKGROUND OF THE INVENTION

1. Field of the Invention

The present invention relates to the preservation of eye tissue in a defined serumfree medical solution, and more particularly, relates to the preservation and enhancement of human corneal tissue, specified as the time between removal from the donor and transplantation.

2. Description of the Prior Art

Keratoplasty, or the transplantation of the cornea, has been effective in providing visual rehabilitation to many who suffer from corneal disorders. This procedure has been severely hampered by the universally inconsistent availability of donor tissue. The use of 4° C. corneal storage medium containing chondroitin sulfate has positively impacted the availability of quality donor tissue. In the United States 95% of all corneas transplanted are stored in a 4° C. chondroitin sulfate containing medium for up to seven days. After 96 hours of preservation the cornea is attended by epithelial decomposition and loss of corneal clarity, as demonstrated by increased swelling of the corneal stroma. The stromal edema is attributed to both the decreased maintenance of the barrier pump function of the corneal endothelium and barrier function of the corneal epithelium.

An alternative to 4° C. corneal storage is the use of organ culture. In this method of corneal preservation, the cornea is maintained at higher temperatures (31° C.–37° C.) allowing greater metabolic activity of the cornea. The use of organ cultured corneas is mainly supported in Europe. The organ culture system utilizes fetal bovine as a major medium component. Mounting concerns over TSEs (Transmissble Spongiform Encephalopathies) stemming from Bovine Spongiform Encephalophy (BSE) outbreaks, have focused much emphasis on animal derived products and their use in corneal preservation. The replacement of serum components in corneal preservation is a formidable challenge, based on over 350 known chemical components found in serum.

The elevated temperature (31° C.–37° C.) of the organ culture technique increases the metabolic rate of the cornea as compared to corneas stored at 4° C. The corneal storage medium must provide an environment similar to the in vivo situation. A serumfree corneal preservation medium must be completely defined as to supplement the components normally found in serum. A critical evaluation of physiologic parameters such as ionic and amino acid composition, bicarbonate equilibrium, available energy sources, dissolved oxygen levels, nutrient cell supplements, coenzymes and enzyme supplements, nucleotide precursors, hormonal supplements, trace minerals, trace elements, growth factors, osmolality and pH should be observed with respect to each preservation medium. Parameters for extended serumfree organ culture preservation should be defined as to the reversibility of cell damage incurred during storage.

Adult corneal endothelium have a limited regenerative capacity and mitotic figures have been rarely observed in vivo; human corneal endothelium in vivo normally responds to trauma by sliding into the wounded area by cell migration. However, in vivo endothelial cell mitosis has been demonstrated in rabbit, bovine and human endothelium. Autoradiographic thymidine uptake studies after cryowounding or mechanical wounding of corneas in vitro has demonstrated existence of mitotic figures in the endothelial monolayer. These studies were all conducted in the presence of serum. Surgical trauma and disease can accelerate the loss of endothelial cells and further compromise the cornea. Thus, the long term preservation and enhancement of the corneal endothelium is a very important aspect of eye bank storage of eye tissue.

An overview of the issues surrounding the storage and handling of corneal tissue is found in Corneal Surgery, chapters 1–4, pages 1–128 edited by Federick S. Brightbill, M.D., published by C. V. Mosby Company, St. Louis, Mo., 1986. A variety of storage media and techniques have been proposed, and current research continues to be directed towards maintaining and actually enhancing the quality of the donor tissues, and increasing the duration of storage of corneal tissues, as defined as the time between excision from a donor and transplantation. Currently, there are no defined serumfree media used in organ culture techniques at 31° C.–38° C.

Accordingly, the present inventions directed towards materials and methods of enhancing ocular tissues, especially corneal tissues, during storage prior to transplantation. One aspect of the invention provides for the enhancement of corneal tissue viability by providing a completely defined serumfree medium that maintains normal physiologic metabolism, and maintains corneal tissue equal to medium that contains serum.

SUMMARY OF THE INVENTION

Organ culture corneal storage at 31° C.–37° C. should provide tissue preservation which is capable of sustaining the functional status of the endothelium. Experimental work has demonstrated that the defined serumfree medical solution is capable of maintaining corneas equal to that of solutions containing serum. The undesirable attributes of storage in serum containing solutions are avoided. The present invention has defined those components that are necessary to maintain corneal tissues during organ culture. The present invention further defines a nutritive solution that provides the corneas with a glycosaminoglycan(s), a detergescent agent(s), an energy source(s), a buffer system (s), an antioxidant(s), membrane stabilizing agents, an antibiotic(s) and/or antimycotic agent(s), ATP or energy precursors, nutrient cell supplements, coenzymes and enzyme supplements, nucleotide precursors, hormonal supplements, non-essential amino acids, trace minerals, trace elements and a growth factor(s) that enhance cell metabolism, wound healing and cell viability. Cell proliferation is regulated by events leading to DNA synthesis; whether or not a cell proceeds with DNA synthesis or is arrested in the early stages of the cell cycle is dependent upon extracellular conditions. Cellular metabolism can be enhances by the addition of essential nutritive components by increasing hexose transport, protein synthesis, amino acid and ion transport.

The novel defined nutrient containing solutions are serumfree. These solutions are able to be used as human corneal preservation solutions, that maintain human corneas equal to solutions containing serum. While serum-supplemented solutions can stimulate mitosis in human corneal cells in tissue culture, the presence of serum in products for use with tissues for human transplantation presents many disadvantages. Serum can be an agent for the transmission of many diseases, such as viral diseases, most notably TSEs (Transmissible Spongiform Encephalopathies). Non-human-derived serum contains many substances capable of eliciting an immune response, and all sera contain some substances such as endotoxins, and growth factors that actually retard cell mitosis. Corneal preservation solutions are well known. Commercially available serumfree corneal storage media for 4° C. preservation consist of Optisol and Optisol-GS are available from Bausch and Lomb, Surgical (Irvine, Calif.). These medium were developed by D. L. Skelnik, B.S., and R. L. Lindstrom, M.D. Commercially available serum containing medium for organ culture are available from Opsia (France). No serumfree media for organ culture are available or in current use.

Nutrient and electrolyte solutions are well defined in the art of tissue culturing. Such solutions contain the essential nutrients and electrolytes at minimal concentrations necessary for cell maintenance and cell growth. The actual compositions of the solutions may vary greatly. In general, they contain inorganic salts, such as calcium magnesium, iron, sodium and potassium salts of carbonates, nitrates, phosphates, chloride, and the like, essential and non-essential amino acids and other essential nutrients. Chemically defined basal nutrient media are available, for example, from Gibco BRL (Grand Island, N.Y.) and Sigma (St. Louis, Mo.) under the names Minimal Essential Medium and TC199. Corneal storage solutions have been adapted from these nutrient media. The defined serumfree medical solution base of the present invention is composed of components found in both MEM and TC199 supplemented with glycosaminoglycan(s), a deturgescent agent(s), an energy source(s), a buffer system(s), an antioxidant(s), membrane stabilizing agents, an antibiotic(s) and/or antimycotic agent (s), ATP or energy precursors, nutrient cell supplements, coenzymes and enzyme supplements, nucleotide precursors, hormonal supplements, non-essential amino acids, trace minerals, trace elements and a growth factor(s).

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
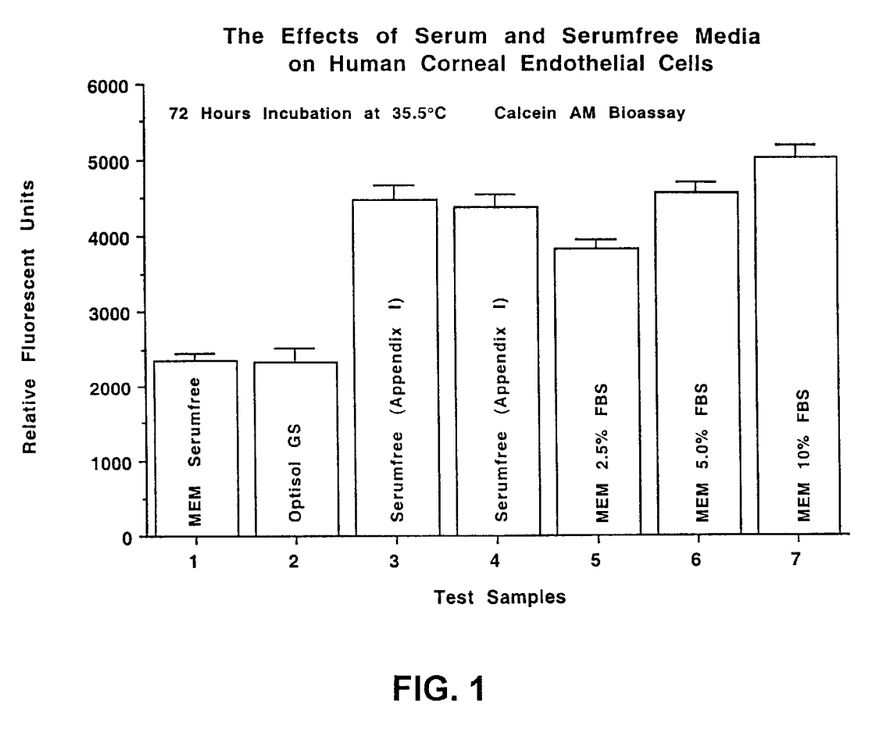
FIG. 1—The Effects of Serum and Serumfree Media on Human Corneal Endothelial Cells.

FIG. 1—Preferred defined serumfree medical solutions for use in the composition and methods of this invention contain an aqueous nutrient and electrolyte solution (e.g. Minimal Essential Medium and/or TC199 medium; a glycosaminoglycan (e.g. chondroitin sulfate, dermatin sulfate, heparin sulfate, heparan sulfate, keratan sulfate and/or hyaluronic acid) in the range of 0.001 mg/ml to 1.0 gram/ml; a deturgescent agent (e.g. dextran, dextran sulfate, hydroxypropylmethyl cellulose, carboxymethylcellulose, cell gum, sodium alginate, albumin, hydroxyethyl starch, hydroxyethyl cellulose, dextrose, glucose and/or cyclodextrin) in the range of 0.001 mg/ml to 1.0 gram/ml; an energy source (glucose, pyruvate, sucrose, fructose and/or dextrose) in a range of 0.01 mM to 10 mM; a buffer system (e.g. sodium bicarbonate, sodium acetate, sodium citrate, sodium phosphate and/or HEPES buffer) in a range of 0.01 mM to 10 mM; an antioxidant (e.g. L-ascorbic acid, 2-mercaptoethanol, glutathione, alpha-tocopherol, alpha-tocopherol acetate, alpha-tocopherol phosphate, and/or selenium) in a range of 0.001 $\mu$M to 10 mM; a membrane stabilizing component (e.g. vitamin A, vitamin B, retinoic acid, trans-retinoic acid, retinol acetate, ethanolamine, phosphoethanolamine, transferrin, lecithin, B-sitosterol and/or L-$\alpha$-phosphatidyl choline) in a range of 0.001 pg/ml to 500 mg/ml; h. an antibiotic an/or antimycotic (e.g. gentamycin, kanamycin, neomycin, vancomycin, tobramycin, clindamycin, streptomycin, levofloxacin, penicillin, cyclosporin, amphotericin B and/or nystatin) in the range of 0.001 $\mu$g/ml to 100 mg/ml; ATP or energy precursors (e.g. adenosine, inosine, adenine, flavin adenine dinucleotide, uridine 5'-triphosphate Na, 5' methylcytosine, B-NAD and/or B-NADP Na) in the range of 0.001 mM to 10 mM; nutrient cell supplements (e.g. alynyl-glutamine, glycyl-glutamine, L-amino-n-butyric acid, L-arginine, D-biotin, betaine HCl, D-carnitine, calciferol, carotene, cholesterol, L-cystine, L-cystiene, L-glutamic acid, D-glucosamine, glucuronate, D-glucuronolactone, L-hydroxyproline, hypoxanthine, L-inositol, glycine, L-ornithine, L-proline, L-serine, myo-inositol, menadione, niacin, nicotinic Acid, p-amino benzoic acid, D-panthothenic Acid, pyridoxal-5-phosphate, pyridoxine HCl, taurine, thymidine, xanthine and or vitamin B12) in a range of 0.001 $\mu$M to 10 mM; coenzymes and enzyme supplements (e.g. acetyl coenzyme A, cocarboxylase, coenzyme A, coenzyme Q10 and/or coenzyme K) in a range of 0.001 $\mu$M to 10 mM; nucleotide precursors (e.g. 2' deoxyadenosine, 2' deoxycytidine HCL, 2' deoxyguanosine, 2-deoxy-D-ribose and/or D-ribose) in a range of 0.001 $\mu$M to 10 mM; hormonal supplements (e.g. B-estradiol, progesterone, testosterone, cortisol, corticosterone, thyroxine, thyroid stimulating hormone and/or calcitonin) in a range of 0.001 pg/ml to 0.100 mg/ml; non-essential amino acids (e.g. L-alanine, L-asparagine, L-aspartic acid, L-glutamic acid, glycine, L-proline and/or L-serine) in the range of 0.001 $\mu$g/ml to 100 mg/ml; trace minerals and trace elements (e.g. $CuSO_4$ $5H_2O$, $ZnSO_4$ $7H_2O$, Selenite Na, Ferric citrate, $MnSO_4$ $H_2O$, $NaSlO_3$ $9H_2O$, molybdic acid, $NH_4VO_3$, $NiSO_4$ $6H_2O$, $SnCl_2$, $AgNO_3$, $Ba(C_2H_3O2)_2$, KBr, $CdCl_2$, $CoCl_2$, $CrCl_3$, NaF, $GeO_2$, KL, RbCl, $ZrOCl_2 8H_2O$) in the range of 0.001 pg/ml to 0.100 mg/ml; p. Growth factors (animal, animal recombinant, human recombinant or natural); (PDGF-BB, PDGF-AA, Nerve growth factor, Nerve growth factor, Stem cell factor, Transforming growth factor-$\alpha$, Transforming growth factor-B, Vascular endothelial growth factor, B-endothelial cell growth factor, Epidermal growth factor, Epithelial neutrophil activating peptide, Heparin binding EGF-like growth factor, Fibroblastic growth factor-acidic, Fibroblastic growth factor-basic, IGF-I, IGF-II, Keratinocyte growth factor, Platelet-derived endothelial cell growth factor, Insulin) in the range of 0.001 pg/ml to 0.100 mg/ml.

The serumfree medical solution of this invention is composed of a defined aqueous nutrient and electrolyte solution, supplemented with a glycosaminoglycan(s), a deturgescent agent(s), an energy source(s), a buffer system(s), an antioxidant(s), membrane stabilizing agents, an antibiotic(s) and/or antimycotic agent(s), ATP or energy precursors, nutrient cell supplements, coenzymes and enzyme supplements, nucleotide precursors, hormonal supplements, non-essential amino acids, trace minerals, trace elements and a growth factor(s) in the amounts sufficient to enhance cell metabolism, cell viability and wound healing following organ culture storage. The excised corneas are aseptically transferred to containers of the corneal storage solution, which are then sealed. For storage these corneas are stored at (2° C. to 38° C.) optimally at 31° C.–37° C.). These corneas are stored for up to 28 days, changing the medium at day 14. At the time of transplantation the corneas are thinned down with solution containing a deturgescent agent. At the time of transplantation, normal corneal deturgescence is maintained intraoperatively and post-operatively. Endothelial function and metabolism is maintained, permitting permanent hydration of the cornea, and thus constant thickness and transparency post operatively. In addition to providing a viable cornea for transplantation, wound healing is potentiated. Various modifications can be made to the present invention without departing from the apparent scope thereof. For instance, the serumfree medical solution can be used in any medical application, and is not strictly limited to ophthalmology. The invention is further illustrated by the following examples, which is not intended to be limiting.

MODE OF OPERATION

Organ culture preservation should provide tissue preservation capable of sustaining the functional status of the corneal endothelium. Each of the components listed in Appendix I were tested in cell culture models with human corneal endothelium, human corneal stromal keratocytes and human corneal epithelial cells to determine optimal concentrations. The following examples are based on the final formulation to illustrate the effect that the formulation had on these cell types. Once the optimum concentrations were derived in cell culture models, test formulations were then tested on human corneas.

Example One

The Effects of A Defined Serumfree Medical Solution and Serum Containing Medium On Human Corneal Endothelial Cells Standard organ culture medium utilizes MEM supplemented with 2.0% fetal bovine serum. A serumfree medium that is to be used for organ culture must support human corneal endothelial cell growth equal to MEM supplemented with 2.0% FBS. This study was conducted to evaluate the defined serumfree medical solution (Appendix I) for human corneal endothelial cell growth against serumfree MEM, MEM containing 2.5% FBS, 5.0% FBS, 10% FBS and commercial Optisol-GS. The test solutions were evaluated in a fluorogenic Calcein AM bioassay with human corneal endothelial cells (HCE). Isolation techniques developed in our laboratory have enabled the establishment of primary and subsequent subcultures of human corneal endothelial cells. In vitro conditions maintain these human corneal endothelial cells in a proliferative state, actively undergoing mitosis. Cell culture offers a model system in which these cells can be studied. A quantitative bioassay has been developed to determine the effects of various test solutions on the stimulation or inhibition of cell division of endothelial cells as measured by Calcein esterase quantitation. A fluorogenic Calcein AM bioassay was used to measure total esterase enzyme activity that is directly proportional to cell number. A Wilcoxen Signed-Rank Test was used to evaluate statistical significance (p<0.05) between the test and control groups. This study was performed at Insight Biomed, Inc., Minneapolis, Minn.

Calcein AM Fluorescent Quantitative Bioassay

Live cells are distinguished by the presence of ubiquitous intracellular esterase activity, determined by the enzymatic conversion of the virtually non-fluorescent cell permeant calcein AM to the intensely fluorescent calcein. The polyanionic calcein is well retained within live cells, producing an intense uniform green (530 nm) fluorescence in live cells.

Calcein AM (Non-Fluorescent)+Esterases=Calcein (Fluorescent Product)

Calcein, which is the esterase product of Calcein AM, is a polar fluorescein derivative that is better retained by viable cells and is 2.5 times brighter than BCECF. The excitation and emission maxima are 485 nm and 530 nm respectively.

Human Corneal Endothelial Cell Cultures

Ninety-six well tissue culture plates were seeded with $1 \times 10^3$ cells/well in a final volume of 200 $\mu l$ of designated medium. Third passage HCE cells were maintained in a humidified incubator at 35.5° C. in a 95% air: 5% $CO_2$ atmosphere. After 1 day of incubation in CSM, supplemented with 10% fetal bovine serum, the medium was removed. The cells were then rinsed one time and incubated with the appropriate test or control solutions. HCE cells were incubated for 72 hours. At the end of each time interval, each well was then rinsed two times with 200 $\mu l$ of Dulbecco's modified phosphate buffered saline. HCE cells were then incubated with 100 $\mu l$/well of 2 $\mu M$ Calcein AM solution (Molecular Probes, Inc. Eugene, Oreg.) and immediately read on a Millipore CytoFluor™ 2300 Fluorescence Measurement System. A 485/20 nm excitation wavelength and the 530125 nm emission wavelength filter set (sensitivity 5) was used to measure the fluorescent product. A Wilcoxen Signed-Rank Test was used to evaluate statistical significance (p<0.05) between the test and control groups.

| Results Statistical Significance as compared to 2.5% (p <0.05) | | | | |
|---|---|---|---|---|
| | RFU | | | |
| MEM | 2356 ± 96 | Yes | .0022 | less than |
| OPTISOL-GS | 2339 ± 184 | Yes | .0022 | less than |
| Serumfree (Appendix I) | 4460 ± 205 | Yes | .0022 | greater than |
| Serumfree (Appendix I) | 4474 ± 168 | Yes | .0022 | greater than |
| MEM 2.5% FBS | 3832 ± 122 | | | |
| MEM 5.0% FBS | 4554 ± 141 | Yes | .0022 | greater than |
| MEM 10% FBS | 5031 ± 163 | Yes | .0022 | greater than |

Discussion

This study was conducted to evaluate the defined serumfree medical solution (Appendix I) for human corneal endothelial cell growth against serumfree MEM, MEM containing 2.5% FBS, 5.0% FBS, 10% FBS and commercial Optisol-GS. The test solutions were evaluated in a fluorogenic Calcein AM bioassay with human corneal endothelial cells (HCE). A quantitative bioassay has been developed to determine the effects of various test solutions on the stimulation or inhibition of cell division of endothelial cells as measured by Calcein esterase quantitation. A fluorogenic Calcein AM bioassay was used to measure total esterase enzyme activity that is directly proportional to cell number. A Wilcoxen Signed-Rank Test was used to evaluate statistical significance (p<0.05) between the test and control groups.

Human corneal endothelial cells incubated with solutions MEM and Optisol GS exhibited a statistically significant decrease in total Calcein fluorescence as compared to the MEM 2.5% FBS control medium. Human corneal endothelial cells incubated with defined serumfree medical solutions (Appendix I) exhibited a statistically significant increase in total Calcein fluorescence as compared to the MEM 2.5% FBS control medium. Human corneal endothelial cells incubated with MEM 5.0% FBS and MEM 10.0% FBS exhibited a statistically significant increase in total Calcein fluorescence as compared to the MEM 2.5% FBS control medium. In conclusion from this data the defined serumfree medical solution (Appendix I) was capable of maintaining total Calcein fluorescence (total number of HCE cells) statistically greater than MEM 2.5% FBS control medium. Therefore, this solution is acceptable for use in organ culture as a corneal preservation solution for human corneal transplantation as defined by the parameters of this bioassay.

Example Two

A Comparative Study of A Serumfree Medical Solution and Standard MEM 2% FBS Medium With Human Corneas Human donor corneas were immersed in 1% povidone iodine in normal saline for three minutes, followed by a one-minute immersion in normal saline. The globes were then rinsed with 12 cc of normal saline with a syringe fitted with a 18-gauge needle. Twenty paired corneas from donors unsuitable for transplantation because of age or cause of death were removed at a certified eye bank an average of 12.0 hours after death and placed in commercial Optisol-GS (Bausch and Lomb, Surgical) at 4° C. Donor globes were transported to the research lab. One of each pair was placed into 100 ml of serumfree (Appendix I) medium. The paired cornea was placed in 50 ml of MEM, containing L-glutamine, HEPES, penicillin, streptomycin, amphotercin B and 2% FBS. Corneas were suspended on a 4.0 silk suture. Each of the bottles containing the corneas were closed and kept at 35° C. for 14 days. At this time, 10 pairs of corneas were removed and placed in appropriate fresh medium and stored for another 14 days. At the 14 day and 28 day time points, corneas stored in serumfree (Appendix I) medium were then placed in commercial Optisol-GS at 35° C. for 24 hours. The paired cornea stored in MEM 2% FBS were placed in MEM containing 6% T500 dextran at 35° C. for 24 hours. Due to the increased hydration of the cornea at elevated temperatures, corneas needed to be thinned down by this procedure. Corneas were evaluated after thinning by the following methods. The corneal thickness was measured by microscopic evaluation with a micrometer. The corneal endothelium was evaluated by staining with 0.1% trypan blue and alizarin red S after the final corneal thickness measurements were taken. Corneal thickness at the 14 day incubation period were 0.386±0.049 mm and 0.479±078 mm, respectively, for the serumfree (Appendix I) medium and MEM 2%. Corneas stored in the serumfree (Appendix I) medium demonstrated a statistically significant ($p<0.05$) decrease in corneal thickness over corneas stored in the MEM 2% FBS medium. Corneas stored in the serumfree (Appendix I) medium had endothelial cell counts of 2716±712 cells/mm$^2$ as compared to 2573±753 cells/mm$^2$ for corneas stored in MEM 2% FBS. There was no statistical difference between these two groups with relation to endothelial cell counts. All endothelial cell monolayers were intact, with normal endothelial cell morphology for both the serumfree (Appendix I) medium and the MEM 2% FBS stored groups. Corneal epithelium was intact for both groups. Corneal thickness at the 28 day incubation period were 0.343±0.015 mm and 0.379±015 mm, respectively, for the serumfree (Appendix I) medium and MEM 2%. Corneas stored in the serumfree (Appendix I) medium demonstrated a statistically significant ($p<0.05$) decrease in corneal thickness over corneas stored in the MEM 2% FBS medium. Corneas stored in the serumfree (Appendix I) medium had endothelial cell counts of 2451±617 cells/mm$^2$ as compared to 2422±570 cells/mm$^2$ for corneas stored in MEM 2% FBS. There was no statistical difference between these two groups with relation to endothelial cell counts. All endothelial cell monolayers were intact, with normal endothelial cell morphology for both the serumfree (Appendix I) medium and the MEM 2% FBS stored groups. Corneal epithelium was intact for both groups.

In conclusion, from the results of this comparative study, corneas stored for both 14 and 28 days in serumfree (Appendix I) medium were able to maintain viable corneal endothelium equal in performance to corneas stored in MEM 2% FBS. This serumfree (Appendix I) medium was effective in maintaining normal corneal cell function and metabolism. Therefore, this serumfree (Appendix I) medium is therefore, acceptable for use as an organ culture preservation medium.

Various modifications can be made to the present invention without departing from the apparent scope hereof.

It is claimed:

1. A defined serumfree medical solution for use at physiological temperatures comprising effective amounts of:
  a. an aqueous nutrient and electrolyte solution;
  b. a glycosaminoglycan;
  c. a deturgescent agent;
  d. an energy source;
  e. a buffer system;
  f. an antioxidant;
  g. membrane stabilizing agents;
  h. at least one member of the group consisting of antibiotic and antimycotic agents;
  i. at least one of the group consisting of ATP and energy precursors;
  j. nutrient cell supplements;
  k. at least one member of the group consisting of coenzymes and enzyme supplements;
  l. at least one nucleotide precursor;
  m. at least one hormonal supplement;
  n. non-essential amino acids;
  o. at least one member of the group consisting of trace minerals and trace elements; and,
  p. at least one growth factor selected from the group consisting of:
    (1) animal natural growth factors;
    (2) animal recombinant growth factors;
    (3) human natural growth factors; and,
    (4) human recombinant growth factors.

2. A defined serumfree medical solution containing components which maintain and enhance the preservation of eye tissues at temperatures from about 2° C. to about 38° C. with a physiological pH, the solution comprising effective amounts of:
  a. an aqueous nutrient and electrolyte solution;
  b. a glycosaminoglycan;
  c. a deturgescent agent;
  d. an energy source;
  e. a buffer system;
  f. an antioxidant;

g. membrane stabilizing agents;

h. at least one member of the group consisting of antibiotic and antimycotic agents;

i. at least one of the group consisting of ATP and energy precursors;

j. nutrient cell supplements;

k. at least one member of the group consisting of coenzymes and enzyme supplements;

l. at least one nucleotide precursor;

m. at least one hormonal supplement;

n. non-essential amino acids;

o. at least one member of the group consisting of trace minerals and trace elements; and, p. at least one growth factor selected from the group consisting of:
   (1) animal natural growth factors;
   (2) animal recombinant growth factors;
   (3) human natural growth factors; and,
   (4) human recombinant growth factors.

3. A defined serumfree medical solution containing components which maintain and enhance the preservation of eye tissues at temperatures from about 16° C. to about 38° C. with a physiological pH, the solution comprising effective amounts of:

a. an aqueous nutrient and electrolyte solution;

b. a glycosaminoglycan;

c. a deturgescent agent;

d. an energy source;

e. a buffer system;

f. an antioxidant;

g. membrane stabilizing agents;

h. at least one member of the group consisting of antibiotic and antimycotic agents;

i. at least one of the group consisting of ATP and energy precursors;

j. nutrient cell supplements;

k. at least one member of the group consisting of coenzymes and enzyme supplements;

l. at least one nucleotide precursor;

m. at least one hormonal supplement;

n. non-essential amino acids;

o. at least one member of the group consisting of trace minerals and trace elements; and, p. at least one growth factor selected from the group consisting of:
   (1) animal natural growth factors;
   (2) animal recombinant growth factors;
   (3) human natural growth factors; and,
   (4) human recombinant growth factors.

4. The defined serumfree medical solution of claim 1, wherein the solution comprises effective amounts of:

a. an aqueous nutrient and electrolyte solution selected from the group consisting of:
   (1) Minimal Essential Medium (MEM);
   (2) TC199 medium; and,
   (3) a combination of Minimal Essential Medium (MEM) and TC199 medium;

b. a glycosaminoglycan in the range of 0.001 mg/ml to 1.0 gram/ml selected from the group consisting of:
   (1) chondroitin sulfate;
   (2) dermatin sulfate;
   (3) heparin sulfate;
   (4) heparan sulfate;
   (5) keratan sulfate; and,
   (6) hyaluronic acid;

c. a deturgescent agent in the range of 0.001 mg/ml to 1.0 gram/ml selected from the group consisting of:
   (1) dextran;
   (2) dextran sulfate;
   (3) hydroxypropylmethyl cellulose;
   (4) carboxymethylcellulose;
   (5) cell gum;
   (6) sodium alginate;
   (7) albumin;
   (8) hydroxyethyl starch;
   (9) hydroxethyl cellose;
   (10) dextrose;
   (11) glucose; and,
   (12) cyclodextrin;

d. an energy source in a range of 0.01 mM to 10 mM selected from the group consisting of:
   (1) glucose;
   (2) pyruvate;
   (3) sucrose;
   (4) fructose; and,
   (5) dextrose;

e. a buffer system in a range of 0.01 mM to 10 mM selected from the group consisting of:
   (1) sodium bicarbonate buffer;
   (2) sodium acetate buffer;
   (3) sodium citrate buffer;
   (4) sodium phosphate buffer; and,
   (5) HEPES buffer;

f. an antioxidant in a range of 0.001 $\mu$M to 10 mM selected from the group consisting of:
   (1) L-ascorbic acid;
   (2) 2-mercaptoethanol;
   (3) glutathione;
   (4) alpha-tocopherol;
   (5) alpha-tocopherol acetate;
   (6) alpha-tocopherol phosphate; and,
   (7) selenium;

g. a membrane stabilizing component in a range of 0.001 pg/ml to 500 mg/ml selected from the group consisting of:
   (1) vitamin A;
   (2) vitamin B;
   (3) retinoic acid;
   (4) trans-retinoic acid;
   (5) retinol acetate;
   (6) ethanolamine;
   (7) phosphoethanolamine;
   (8) transferrin;
   (9) lecithin;
   (10) B-sitosterol; and,
   (11) L-$\alpha$-phosphatidyl choline;

h. an agent, having antibiotic, antimycotic, or antibiotic and antimycotic activity, in the range of 0.001 $\mu$g/ml to 100 mg/ml selected from the group consisting of:
   (1) gentamycin;
   (2) kanamycin;
   (3) neomycin;
   (4) vancomycin;
   (5) tobramycin;
   (6) clindamycin;
   (7) streptomycin;
   (8) levofloxacin;
   (9) penicillin;

(10) cyclosporin;
(11) amphotericin B; and,
(12) nystatin;
i. ATP or energy precursors in the range of 0.001 mM to 10 mM selected from the group consisting of:
(1) adenosine;
(2) inosine;
(3) adenine;
(4) flavin adenine dinucleotide;
(5) uridine 5'-triphosphate Na;
(6) 5' methylcytosine;
(7) B-NAD; and,
(8) B-NADP Na;
j. nutrient cell supplements in a range of 0.001 $\mu$M to 10 mM selected from the group consisting of:
(1) alynyl-glutamine;
(2) glycyl-glutamine;
(3) L-amino-n-butyric acid;
(4) L-arginine;
(5) D-biotin;
(6) Betaine HCl;
(7) D-carnitine;
(8) calciferol;
(9) carotene;
(10) cholesterol;
(11) L-cystine;
(12) L-cystiene;
(13) L-glutamic acid;
(14) D-glucosamine;
(15) glucuronate;
(16) D-Glucuronolactone;
(17) L-hydroxyproline;
(18) hypoxanthine;
(19) L-inositol;
(20) Glycine;
(21) L-ornithine;
(22) L-proline;
(23) L-serine;
(24) myo-inositol;
(25) Menadione;
(26) niacin;
(27) nicotinic Acid;
(28) p-amino benzoic acid;
(29) D-Panthothenic Acid;
(30) pyridoxal-5-phosphate;
(31) pyridoxine HCl;
(32) taurine;
(33) thymidine;
(34) xanthine; and,
(35) Vitamin B12;
k. coenzymes and enzyme supplements in a range of 0.001 $\mu$M to 10 mM selected from the group consisting of:
(1) acetyl Coenzyme A;
(2) cocarboxylase;
(3) coenzyme A;
(4) coenzyme Q10; and,
(5) coenzyme K;
l. nucleotide precursors in a range of 0.001 $\mu$M to 10 mM selected from the group consisting of:
(1) 2' Deoxyadenosine;
(2) 2' Deoxycytidine HCl;
(3) 2' Deoxyguanosine;
(4) 2-deoxy-D-ribose; and,
(5) D-ribose;
m. hormonal supplements in a range of 0.001 pg/ml to 0.100 mg/ml selected from the group consisting of:

(1) B-estradiol;
(2) progesterone;
(3) testosterone;
(4) cortisol;
(5) Corticosterone;
(6) thyroxine;
(7) thyroid stimulating hormone; and,
(8) calcitonin;
n. non-essential amino acids in the range of 0.001 $\mu$g/ml to 100 mg/ml selected from the group consisting of:
(1) L-alanine;
(2) L-asparagine;
(3) L-aspartic acid;
(4) L-glutamic acid;
(5) glycine;
(6) L-proline; and,
(7) L-serine;
o. trace minerals and trace elements in the range of 0.001 pg/ml to 0.100 mg/ml selected from the group consisting of:
(1) $CuSO_4.5H_2O$
(2) $ZnSO_4.7H_2O$;
(3) Selenite Na;
(4) Ferric citrate;
(5) $MnSO_4.H_2O$;
(6) $NaSiO_3.9H_2O$;
(7) molybdic acid;
(8) $NH_4VO_3$;
(9) $NiSO_4.6H_2O$;
(10) $SnCl_2$;
(11) $AgNO_3$;
(12) $Ba(C_2H_3O_2)_2$;
(13) KBr;
(14) $CdCl_2$;
(15) $CoCl_2$;
(16) $CrCl_3$;
(17) NaF;
(18) $GeO_2$;
(19) KI;
(20) RbCl; and,
(21) $ZrOCl_2.8H_2O$; and,
p. growth factors in the range of 0.001 pg/ml to 0.100 mg/ml selected from the group consisting of:
(1) PDGF-BB;
(2) PDGF-AA;
(3) nerve growth factor;
(4) nerve growth factor B;
(5) stem cell factor;
(6) transforming growth factor-$\alpha$;
(7) transforming growth factor-B;
(8) vascular endothelial growth factor;
(9) B-endothelial cell growth factor;
(10) epidermal growth factor;
(11) epithelial neutrophil activating peptide;
(12) heparin binding EGF-like growth factor;
(13) fibroblastic growth factor-acidic;
(14) fibroblastic growth factor-basic;
(15) IGF-I;
(16) IGF-II;
(17) keratinocyte growth factor;
(18) platelet-derived endothelial cell growth factor;
(19) insulin; and,
(20) hepatocyte growth factor.

5. A defined serumfree medical solution which maintains and enhances the preservation of eye tissues at temperatures from about 16° C. to about 38° C. with a physiological pH, the solution comprising:

a. an aqueous nutrient and electrolyte solution selected from the group consisting of:
   (1) Minimal Essential Medium (MEM);
   (2) TC199 medium; and,
   (3) a combination of Minimal Essential Medium (MEM) and TC199 medium;
b. a glycosaminoglycan in the range of 0.001 mg/ml to 1.0 gram/ml selected from the group consisting of:
   (1) chondroitin sulfate;
   (2) dermatin sulfate;
   (3) heparin sulfate;
   (4) heparan sulfate;
   (5) keratan sulfate; and,
   (6) hyaluronic acid;
c. a deturgescent agent in the range of 0.001 mg/ml to 1.0 gram/ml selected from the group consisting of:
   (1) dextran;
   (2) dextran sulfate;
   (3) hydroxypropylmethyl cellulose;
   (4) carboxymethylcellulose;
   (5) cell gum;
   (6) sodium alginate;
   (7) albumin;
   (8) hydroxyethyl starch;
   (9) hydroxethyl cellose;
   (10) dextrose;
   (11) glucose; and,
   (12) cyclodextrin;
d. an energy source in a range of 0.01 mM to 10 mM selected from the group consisting of:
   (1) glucose;
   (2) pyruvate;
   (3) sucrose;
   (4) fructose; and,
   (5) dextrose;
e. a buffer system in a range of 0.01 mM to 10 mM selected from the group consisting of:
   (1) sodium bicarbonate buffer;
   (2) sodium acetate buffer;
   (3) sodium citrate buffer;
   (4) sodium phosphate buffer; and,
   (5) HEPES buffer;
f. an antioxidant in a range of 0.001 $\mu$M to 10 mM selected from the group consisting of:
   (1) L-ascorbic acid;
   (2) 2-mercaptoethanol;
   (3) glutathione;
   (4) alpha-tocopherol;
   (5) alpha-tocopherol acetate;
   (6) alpha-tocopherol phosphate; and,
   (7) selenium;
g. a membrane stabilizing component in a range of 0.001 pg/ml to 500 mg/ml selected from the group consisting of:
   (1) vitamin A;
   (2) vitamin B;
   (3) retinoic acid;
   (4) trans-retinoic acid;
   (5) retinol acetate;
   (6) ethanolamine;
   (7) phosphoethanolamine;
   (8) transferrin;
   (9) lecithin;
   (10) B-sitosterol; and,
   (11) L-$\alpha$-phosphatidyl choline;
h. an agent, having antibiotic, antimycotic, or antibiotic and antimycotic activity, in the range of 0.001 $\mu$g/ml to 100 mg/ml selected from the group consisting of:
   (1) gentamycin;
   (2) kanamycin;
   (3) neomycin;
   (4) vancomycin;
   (5) tobramycin;
   (6) clindamycin;
   (7) streptomycin;
   (8) levofloxacin;
   (9) penicillin;
   (10) cyclosporin;
   (11) amphotericin B; and,
   (12) nystatin;
i. ATP or energy precursors in the range of 0.001 mM to 10 mM selected from the group consisting of:
   (1) adenosine;
   (2) inosine;
   (3) adenine;
   (4) flavin adenine dinucleotide;
   (5) uridine 5'-triphosphate Na;
   (6) 5' methylcytosine;
   (7) B-NAD; and,
   (8) B-NADP Na;
j. nutrient cell supplements in a range of 0.001 $\mu$M to 10 mM selected from the group consisting of:
   (1) alynyl-glutamine;
   (2) glycyl-glutamine;
   (3) L-amino-n-butyric acid;
   (4) L-arginine;
   (5) D-biotin;
   (6) Betaine HCl;
   (7) D-carnitine;
   (8) calciferol;
   (9) carotene;
   (10) cholesterol;
   (11) L-cystine;
   (12) L-cystiene;
   (13) L-glutamic acid;
   (14) D-glucosamine;
   (15) glucuronate;
   (16) D-Glucuronolactone;
   (17) L-hydroxyproline;
   (18) hypoxanthine;
   (19) L-inositol;
   (20) Glycine;
   (21) L-ornithine;
   (22) L-proline;
   (23) L-serine;
   (24) myo-inositol;
   (25) Menadione;
   (26) niacin;
   (27) nicotinic Acid;
   (28) p-amino benzoic acid;
   (29) D-Panthothenic Acid;
   (30) pyridoxal-5-phosphate;
   (31) pyridoxine HCl;
   (32) taurine;
   (33) thymidine;
   (34) xanthine; and,
   (35) Vitamin B12;
k. coenzymes and enzyme supplements in a range of 0.001 $\mu$M to 10 mM selected from the group consisting of:
   (1) acetyl Coenzyme A;
   (2) cocarboxylase;
   (3) coenzyme A;
   (4) coenzyme Q10; and,
   (5) coenzyme K;

l. nucleotide precursors in a range of 0.001 µM to 10 mM selected from the group consisting of:
  (1) 2' Deoxyadenosine;
  (2) 2' Deoxycytidine HCl;
  (3) 2' Deoxyguanosine;
  (4) 2-deoxy-D-ribose; and,
  (5) D-ribose;
m. hormonal supplements in a range of 0.001 pg/ml to 0.100 mg/ml selected from the group consisting of:
  (1) B-estradiol;
  (2) progesterone;
  (3) testosterone;
  (4) cortisol;
  (5) Corticosterone;
  (6) thyroxine;
  (7) thyroid stimulating hormone; and,
  (8) calcitonin;
n. non-essential amino acids in the range of 0.001 µg/ml to 100 mg/ml selected from the group consisting of:
  (1) L-alanine;
  (2) L-asparagine;
  (3) L-aspartic acid;
  (4) L-glutamic acid;
  (5) glycine;
  (6) L-proline; and,
  (7) L-serine;
o. trace minerals and trace elements in the range of 0.001 pg/ml to 0.100 mg/ml selected from the group consisting of:
  (1) $CuSO_4.5H_2O$;
  (2) $ZnSO_4.7H_2O$;
  (3) Selenite Na;
  (4) Ferric citrate;
  (5) $MnSO_4.H_2O$;
  (6) $NaSiO_3.9H_2O$;
  (7) molybdic acid;
  (8) $NH_4VO_3$;
  (9) $NiSO_4.6H_2O$;
  (10) $SnCl_2$;
  (11) $AgNO_3$;
  (12) $Ba(C_2H_3O_2)_2$;
  (13) KBr;
  (14) $CdCl_2$;
  (15) $CoCl_2$;
  (16) $CrCl_3$;
  (17) NaF;
  (18) $GeO_2$;
  (19) Kl;
  (20) RbCl; and,
  (21) $ZrOCl_2.8H_2O$; and,
p. growth factors (animal, animal recombinant, human recombinant or natural) in the range of 0.001 pg/ml to 0.100 mg/ml selected from the group consisting of:
  (1) PDGF-BB;
  (2) PDGF-AA;
  (3) nerve growth factor;
  (4) nerve growth factor B;
  (5) stem cell factor;
  (6) transforming growth factor-α;
  (7) transforming growth factor-B;
  (8) vascular endothelial growth factor;
  (9) B-endothelial cell growth factor;
  (10) epidermal growth factor;
  (11) epithelial neutrophil activating peptide;
  (12) heparin binding EGF-like growth factor;
  (13) fibroblastic growth factor-acidic;
  (14) fibroblastic growth factor-basic;
  (15) IGF-I;
  (16) IGF-II;
  (17) keratinocyte growth factor;
  (18) platelet-derived endothelial cell growth factor;
  (19) insulin; and,
  (20) hepatocyte growth factor.

6. The defined serumfree medical solution of claim 5, wherein said composition maintains and enhances the preservation of mammalian eye tissues after coming into contact with said solution.

7. The defined serumfree medical solution of claim 5, wherein said composition maintains and enhances the preservation of mammalian eye tissues after coming into contact with said solution before or after surgical use of a laser.

8. The defined serumfree medical solution of claim 5, wherein said composition maintains and enhances the preservation of mammalian eye tissues after coming into contact with said solution before or after degenerative eye conditions.

9. The defined serumfree medical solution of claim 5, wherein said composition maintains and enhances the preservation of mammalian eye tissues after coming into contact with said solution before or after surgery.

10. The defined serumfree medical solution of claim 5, wherein said composition maintains and enhances the preservation of mammalian tissues after coming into contact with said solution.

11. A serumfree medium for in vitro storage of cornea tissue in keratoplasty, the medium characterized by an ability to maintain cornea tissue viability for 28 days of in vitro storage at a temperature from about 31° C. to about 37° C. with only a single medium replacement at 14 days of in vitro storage.

12. The serumfree medium for in vitro storage of cornea tissue in keratoplasty of claim 11, the medium characterized by an ability to maintain cornea tissue viability during in vitro storage for a time period from about 1 day to about 28 days at a temperature from about 31° C. to about 37° C.

13. The serumfree medium for in vitro storage of cornea tissue in keratoplasty of claim 11, wherein the medium comprises effective amounts of:
  a. an aqueous nutrient and electrolyte solution;
  b. a glycosaminoglycan;
  c. a deturgescent agent;
  d. an energy source;
  e. a buffer system;
  f. an antioxidant;
  g. at least one membrane stabilizing agent;
  h. at least one antibiotic or antimycotic agent;
  i. precursor of ATP or other energy precursor;
  j. at least one nutrient cell supplement;
  k. at least one coenzyme and enzyme supplement;
  l. at least one nucleotide precursor;
  m. at least one hormonal supplement;
  n. at least one non-essential amino acid;
  o. at least one trace mineral and trace element; and,
  p. at least one growth factor, wherein said at least one growth factor may originate from a source selected from the group consisting of:
    (1) natural animal;
    (2) natural human;
    (3) recombinant animal; and,
    (4) recombinant human growth factors.

14. The serumfree medium for in vitro storage of cornea tissue in keratoplasty of claim 13, wherein the aqueous nutrient and electrolyte solution comprises an aqueous nutrient and electrolyte solution from the group consisting of:
  a. Minimal Essential Medium (MEM);
  b. TC199 medium; and,
  c. a combination of Minimal Essential Medium (MEM) and TC199 medium.

15. The serumfree medium for in vitro storage of cornea tissue in keratoplasty of claim 13, wherein the glycosaminoglycan comprises a glycosaminoglycan in the range of 0.001 mg/ml to 1.0 gram/ml selected from the group consisting of:
  a. chondroitin sulfate;
  b. dermatin sulfate;
  c. heparin sulfate;
  d. heparan sulfate;
  e. keratan sulfate; and,
  f. hyaluronic acid.

16. The serumfree medium for in vitro storage of cornea tissue in keratoplasty of claim 13, wherein the deturgescent agent comprises a deturgescent agent in the range of 0.001 mg/ml to 1.0 gram/ml selected from the group consisting of:
  a. dextran;
  b. dextran sulfate;
  c. hydroxypropylmethyl cellulose;
  d. carboxymethylcellulose;
  e. cell gum;
  f. sodium alginate;
  g. albumin;
  h. hydroxyethyl starch;
  i. hydroxethyl cellose;
  j. dextrose;
  k. glucose; and,
  l. cyclodextrin.

17. The serumfree medium for in vitro storage of cornea tissue in keratoplasty of claim 13, wherein the energy system comprises an energy source in a range of 0.01 mM to 10 mM selected from the group consisting of:
  a. glucose;
  b. pyruvate;
  c. sucrose;
  d. fructose; and,
  e. dextrose.

18. The serumfree medium for in vitro storage of cornea tissue in keratoplasty of claim 13, wherein the buffer system comprises a buffer system in a range of 0.01 mM to 10 mM selected from the group consisting of:
  a. sodium bicarbonate buffer;
  b. sodium acetate buffer;
  c. sodium citrate buffer;
  d. sodium phosphate buffer; and,
  e. HEPES buffer.

19. The serumfree medium for in vitro storage of cornea tissue in keratoplasty of claim 13, wherein the antioxidant comprises an antioxidant in a range of 0.001 $\mu$M to 10 mM selected from the group consisting of:
  a. L-ascorbic acid;
  b. 2-mercaptoethanol;
  c. glutathione;
  d. alpha-tocopherol;
  e. alpha-tocopherol acetate;
  f. alpha-tocopherol phosphate; and,
  g. selenium.

20. The serumfree medium for in vitro storage of cornea tissue in keratoplasty of claim 13, wherein the membrane stabilizing agent comprises a membrane stabilizing component in a range of 0.001 pg/ml to 500 mg/ml selected from the group consisting of:
  a. vitamin A;
  b. vitamin B;
  c. retinoic acid;
  d. trans-retinoic acid;
  e. retinol acetate;
  f. ethanolamine;
  g. phosphoethanolamine;
  h. transferrin;
  i. lecithin;
  j. B-sitosterol; and,
  k. L-$\alpha$-phosphatidyl choline.

21. The serumfree medium for in vitro storage of cornea tissue in keratoplasty of claim 13, wherein the antibiotic or antimycotic agent is in the range of 0.001 $\mu$g/ml to 100 mg/ml and selected from the group consisting of:
  a. gentamycin;
  b. kanamycin;
  c. neomycin;
  d. vancomycin;
  e. tobramycin;
  f. clindamycin;
  g. streptomycin;
  h. levofloxacin;
  i. penicillin;
  j. cyclosporin;
  k. amphotericin B; and,
  l. nystatin.

22. The serumfree medium for in vitro storage of cornea tissue in keratoplasty of claim 13, wherein the ATP or energy precursor is in the range of 0.001 mM to 10 mM and selected from the group consisting of:
  a. adenosine;
  b. inosine;
  c. adenine;
  d. flavin adenine dinucleotide;
  e. uridine 5'-triphosphate Na;
  f. 5' methylcytosine;
  g. B-NAD; and,
  h. B-NADP Na.

23. The serumfree medium for in vitro storage of cornea tissue in keratoplasty of claim 13, wherein the nutrient cell supplement is in a range of 0.001 $\mu$M to 10 mM and selected from the group consisting of:
  a. alynyl-glutamine;
  b. glycyl-glutamine;
  c. L-amino-n-butyric acid;
  d. L-arginine;
  e. D-biotin;
  f. Betaine HCl;
  g. D-carnitine;
  h. calciferol;
  i. carotene;

j. cholesterol;
k. L-cystine;
l. L-cystiene;
m. L-glutamic acid;
n. D-glucosamine;
o. glucuronate;
p. D-Glucuronolactone;
q. L-hydroxyproline;
r. hypoxanthine;
s. L-inositol;
t. Glycine;
u. L-ornithine;
v. L-proline;
w. L-serine;
x. myo-inositol;
y. Menadione;
z. niacin;
aa. nicotinic Acid;
bb. p-amino benzoic acid;
cc. D-Panthothenic Acid;
dd. pyridoxal-5-phosphate;
ee. pyridoxine HCl;
ff. taurine;
gg. thymidine;
hh. xanthine; and,
ii. Vitamin B12.

24. The serumfree medium for in vitro storage of cornea tissue in keratoplasty of claim 13, wherein the coenzyme and enzyme supplement is in the range of 0.001 $\mu$M to 10 mM and selected from the group consisting of:
   a. acetyl Coenzyme A;
   b. cocarboxylase;
   c. coenzyme A;
   d. coenzyme Q10; and,
   e. coenzyme K.

25. The serumfree medium for in vitro storage of cornea tissue in keratoplasty of claim 13, wherein the nucleotide precursor is in the range of 0.001 $\mu$M to 10 mM and selected from the group consisting of:
   a. 2' Deoxyadenosine;
   b. 2' Deoxycytidine HCl;
   c. 2' Deoxyguanosine;
   d. 2-deoxy-D-ribose; and,
   e. D-ribose.

26. The serumfree medium for in vitro storage of cornea tissue in keratoplasty of claim 13, wherein the hormonal supplement is in the range of 0.001 pg/ml to 0.100 mg/ml and selected from the group consisting of:
   a. B-estradiol;
   b. progesterone;
   c. testosterone;
   d. cortisol;
   e. Corticosterone;
   f. thyroxine;
   g. thyroid stimulating hormone; and,
   h. calcitonin.

27. The serumfree medium for in vitro storage of cornea tissue in keratoplasty of claim 13, wherein the non-essential amino acid is in the range of 0.001 $\mu$g/ml to 100 mg/ml and selected from the group consisting of:
   a. L-alanine;
   b. L-asparagine;
   c. L-aspartic acid;
   d. L-glutamic acid;
   e. glycine;
   f. L-proline; and,
   g. L-serine.

28. The serumfree medium for in vitro storage of cornea tissue in keratoplasty of claim 13, wherein the trace minerals and trace element is in the range of 0.001 pg/ml to 0.100 mg/ml and selected from the group consisting of:
   a. $CuSO_4.5H_2O$
   b. $ZnSO_4.7H_2O$;
   c. Selenite Na;
   d. Ferric citrate;
   e. $MnSO_4.H_2O$;
   f. $NaSiO_3.9H_2O$;
   g. molybdic acid;
   h. $NH_4VO_3$;
   i. $NiSO_4.6H_2O$;
   j. $SnCl_2$;
   k. $AgNO_3$;
   l. $Ba(C_2H_3O_2)_2$;
   m. KBr;
   n. $CdCl_2$;
   o. $CoCl_2$;
   p. $CrCl_3$;
   q. NaF;
   r. $GeO_2$;
   s. KI;
   t. RbCl; and,
   u. $ZrOCl_2.8H_2O$.

29. The serumfree medium for in vitro storage of cornea tissue in keratoplasty of claim 13, wherein the growth factor is in the range of 0.001 pg/ml to 0.100 mg/ml and selected from the group consisting of:
   a. PDGF-BB;
   b. PDGF-AA;
   c. nerve growth factor;
   d. nerve growth factor B;
   e. stem cell factor;
   f. transforming growth factor-$\alpha$;
   g. transforming growth factor-B;
   h. vascular endothelial growth factor;
   i. B-endothelial cell growth factor;
   j. epidermal growth factor;
   k. epithelial neutrophil activating peptide;
   l. heparin binding EGF-like growth factor;
   m. fibroblastic growth factor-acidic;
   n. fibroblastic growth factor-basic;
   o. IGF-I;
   p. IGF-II;
   q. keratinocyte growth factor;
   r. platelet-derived endothelial cell growth factor;
   s. insulin; and,
   t. hepatocyte growth factor.

30. A serumfree medium for in vitro storage of cornea tissue in keratoplasty consisting of:

(1) Calcium Chloride 2H$_2$O at a concentration 0.106000 grams per liter;
(2) Calcium Chloride (anhydrous) at a concentration of 0.105511 grams per liter;
(3) Magnesium Sulfate (anhydrous) at a concentration of 0.091526 grams per liter;
(4) Potassium Chloride at a concentration of 0.371023 grams per liter;
(5) Sodium Acetate (anhydrous) at a concentration of 0.012000 grams per liter;
(6) Sodium Chloride at a concentration of 6.069984 grams per liter;
(7) Sodium Phosphate Monobasic (anhydrous) at a concentration of 0.122658 grams per liter;
(8) Ferric Nitrate at a concentration of 0.000301 grams per liter;
(9) L-Alanine at a concentration of 0.017932 grams per liter;
(10) L-Arginine HCl at a concentration of 0.078936 grams per liter;
(11) L-Asparagine H$_2$O at a concentration of 0.012676 grams per liter;
(12) L-Aspartic Acid at a concentration of 0.011944 grams per liter;
(13) L-Cystine 2 HCl at a concentration of 0.021979 grams per liter;
(14) L-Glutamic Acid at a concentration of 0.012124 grams per liter;
(15) L-Glutamine at a concentration of 0.054292 grams per liter;
(16) Glycine at a concentration of 0.009904 grams per liter;
(17) L-Histidine HCl H$_2$O at a concentration of 0.032817 grams per liter;
(18) Hydroxy-L-Proline at a concentration of 0.007629 grams per liter;
(19) L-Isoleucine at a concentration of 0.034649 grams per liter;
(20) L-Leucine at a concentration of 0.035609 grams per liter;
(21) L-Lysine HCl at a concentration of 0.053620 grams per liter;
(22) L-Methionine at a concentration of 0.009689 grams per liter;
(23) L-Ornithine HCl at a concentration of 0.003764 grams per liter;
(24) L-Phenylalanine at a concentration of 0.023494 grams per liter;
(25) L-Proline at a concentration of 0.009352 grams per liter;
(26) L-Serine at a concentration of 0.010600 grams per liter;
(27) L-Threonine at a concentration of 0.032895 grams per liter;
(28) L-Tryptophan at a concentration of 0.012276 grams per liter;
(29) L-Tyrosine 2 Na 2H$_2$O at a concentration of 0.036860 grams per liter;
(30) L-Valine at a concentration of 0.034268 grams per liter;
(31) Adenine sulfate at a concentration of 0.005993 grams per liter;
(32) Adenosine at a concentration of 0.003007 grams per liter;
(33) L-Ascorbic Acid Na at a concentration of 0.020030 grams per liter;
(34) D-Biotin at a concentration of 0.000016 grams per liter;
(35) Calciferol at a concentration of 0.000158 grams per liter;
(36) Choline Chloride at a concentration of 0.001028 grams per liter;
(37) Folic Acid at a concentration of 0.000538 grams per liter;
(38) I-Inositol at a concentration of 0.001055 grams per liter;
(39) Inosine at a concentration of 0.005993 grams per liter;
(40) Myo-Inositol at a concentration of 0.000050 grams per liter;
(41) Menadione (Sodium Bisulfite) at a concentration of 0.000016 grams per liter;
(42) Niacin at a concentration of 0.000015 grams per liter;
(43) Niacinamide at a concentration of 0.000553 grams per liter;
(44) Nicotinic Acid at a concentration of 0.000025 grams per liter;
(45) P-Amino Benzoic Acid at a concentration of 0.000080 grams per liter;
(46) D-Ca Pantothenate at a concentration of 0.000528 grams per liter;
(47) D-Panthothenic Acid (Hemicalcium) at a concentration of 0.000010 grams per liter;
(48) Pyridoxal HCl at a concentration of 0.000553 grams per liter;
(49) Pyridoxine HCl at a concentration of 0.000175 grams per liter;
(50) Retinol Acetate at a concentration of 0.000100 grams per liter;
(51) Riboflavin at a concentration of 0.000063 grams per liter;
(52) Thiamine HCl at a concentration of 0.000538 grams per liter;
(53) DL-α-Tocopherol Phosphate 2 Na at a concentration of 0.000016 grams per liter;
(54) Vitamin B-12 at a concentration of 0.004818 grams per liter;
(55) L-Amino-n-Butyric Acid at a concentration of 0.002204 grams per liter;
(56) Cocarboxylase at a concentration of 0.000400 grams per liter;
(57) Coenzyme A Na at a concentration of 0.001000 grams per liter;
(58) 2'-Deoxyadenosine at a concentration of 0.004000 grams per liter;
(59) 2'-Deoxycytidine HCl at a concentration of 0.004000 grams per liter;
(60) 2'-Deoxyguanosine at a concentration of 0.004000 grams per liter;
(61) Flavin Adenine Dinucleotide 2 Na at a concentration of 0.000400 grams per liter;
(62) D-Glucosamine HCl at a concentration of 0.001540 grams per liter;

(63) D-Glucose at a concentration of 0.927557 grams per liter;
(64) Glucuronate Na at a concentration of 0.000720 grams per liter;
(65) D-Glucuronolactone at a concentration of 0.000720 grams per liter;
(66) Glutathione Na at a concentration of 0.008000 grams per liter;
(67) 5' Methylcytosine HCl at a concentration of 0.000040 grams per liter;
(68) B-NAD at a concentration of 0.002800 grams per liter;
(69) B-NADP Na at a concentration of 0.000400 grams per liter;
(70) Phenol Red Na at a concentration of 0.013276 grams per liter;
(71) Taurine at a concentration of 0.001672 grams per liter;
(72) Thymidine at a concentration of 0.004000 grams per liter;
(73) Tween 80 at a concentration of 0.005000 grams per liter;
(74) Uridine 5'-Triphosphate Na at a concentration of 0.000400 grams per liter;
(75) HEPES at a concentration of 3.143182 grams per liter;
(76) Cholesterol at a concentration of 0.000120 grams per liter;
(77) Sodium Bicarbonate at a concentration of 2.320000 grams per liter;
(78) Sodium Pyruvate at a concentration of 0.0660000 grams per liter;
(79) Gentamycin at a concentration of 0.0900000 grams per liter;
(80) Streptomycin at a concentration of 0.1200000 grams per liter;
(81) 2-Mercaptoethanol at a concentration of 0.3 mM;
(82) Chondroitin Sulfate at a concentration of 3.000000 grams per liter;
(83) L-Ascorbic Acid at a concentration of 0.010566 grams per liter;
(84) L-Alynyl-L-Glutamine at a concentration of 2 mM;
(85) Glutathione Na Reduced at a concentration of 0.307000 grams per liter;
(86) (+)-α-Tocopherol Acetate at a concentration of 0.441120 grams per liter;
(87) Recombinant human insulin at a concentration of 0.006000 grams per liter;
(88) Recombinant human PDGF-BB at a concentration of 0.000200 grams per liter;
(89) B-estradiol at a concentration of 0.000001 grams per liter;
(90) Progesterone at a concentration of 0.000002 grams per liter;
(91) D-Carnitine HCl at a concentration of 0.002500 grams per liter;
(92) Pyridoxal-5-Phosphate at a concentration of 0.001000 grams per liter;
(93) Betaine HCl at a concentration of 0.001250 grams per liter;
(94) L-α-Phosphatidyl Choline at a concentration of 0.000500 grams per liter;
(95) Hypoxanthine at a concentration of 0.000180 grams per liter;
(96) 2-Deoxy-D-Ribose at a concentration of 0.000300 grams per liter;
(97) D-Ribose at a concentration of 0.000300 grams per liter;
(98) Xanthine at a concentration of 0.000206 grams per liter;
(99) $CuSO_4.5H_2O$ at a concentration of $1.60 \times 10^{-06}$ grams per liter;
(100) $ZnSO_4.7H_2O$ at a concentration of $8.63 \times 10^{-04}$ grams per liter;
(101) Selenite Na at a concentration of $1.73 \times 10^{-05}$ grams per liter;
(102) Ferric Citrate at a concentration of $1.16 \times 10^{-03}$ grams per liter;
(103) $MnSO_4.H_2O$ at a concentration of $1.70 \times 10^{-08}$ grams per liter;
(104) $NaSiO_3.9H_2O$ at a concentration of $1.40 \times 10^{-05}$ grams per liter;
(105) Molybdic Acid, Ammonium Salt at a concentration of $1.24 \times 10^{-07}$ grams per liter;
(106) $NH_4VO_3$ at a concentration of $6.50 \times 10^{-08}$ grams per liter;
(107) $NiSO_4.6H_2O$ at a concentration of $1.30 \times 10^{-08}$ grams per liter;
(108) $SnCl_2$ (anhydrous) at a concentration of $1.20 \times 10^{-08}$ grams per liter;
(109) $AlCl_3.6H_2O$ at a concentration of $1.20 \times 10^{-07}$ grams per liter;
(110) $AgNO_3$ at a concentration of $1.70 \times 10^{-08}$ grams per liter;
(111) $Ba(C_2H_3O_2)_2$ at a concentration of $2.55 \times 10^{-07}$ grams per liter;
(112) KBr at a concentration of $1.20 \times 10^{-08}$ grams per liter;
(113) $CdCl_2$ at a concentration of $2.28 \times 10^{-07}$ grams per liter;
(114) $CoCl_2$ at a concentration of $2.38 \times 10^{-07}$ grams per liter;
(115) $CrCl_3$ (anhydrous) at a concentration of $3.20 \times 10^{-08}$ grams per liter;
(116) NaF at a concentration of $4.20 \times 10^{-07}$ grams per liter;
(117) $GeO_2$ at a concentration of $5.30 \times 10^{-08}$ grams per liter;
(118) KI at a concentration of $1.70 \times 10^{-08}$ grams per liter;
(119) RbCl at a concentration of $1.21 \times 10^{-07}$ grams per liter; and,
(120) $ZrOCl_2.8H_2O$ at a concentration of $3.22 \times 10^{-07}$ grams per liter.

31. A method of treating an eye tissue for use in subsequent eye surgery during the period of time elapsing between removal of the eye tissue from an eye tissue donor and implantation of the eye tissue into an eye tissue recipient, the method comprising the step of contacting the eye tissue with a serumfree solution.

32. The method of claim 31, wherein the serumfree solution consists of:
(1) Calcium Chloride $2H_2O$ at a concentration 0.106000 grams per liter;
(2) Calcium Chloride (anhydrous) at a concentration of 0.105511 grams per liter;

(3) Magnesium Sulfate (anhydrous) at a concentration of 0.091526 grams per liter;
(4) Potassium Chloride at a concentration of 0.371023 grams per liter;
(5) Sodium Acetate (anhydrous) at a concentration of 0.012000 grams per liter;
(6) Sodium Chloride at a concentration of 6.069984 grams per liter;
(7) Sodium Phosphate Monobasic (anhydrous) at a concentration of 0.122658 grams per liter;
(8) Ferric Nitrate at a concentration of 0.000301 grams per liter;
(9) L-Alanine at a concentration of 0.017932 grams per liter;
(10) L-Arginine HCl at a concentration of 0.078936 grams per liter;
(11) L-Asparagine $H_2O$ at a concentration of 0.012676 grams per liter;
(12) L-Aspartic Acid at a concentration of 0.011944 grams per liter;
(13) L-Cystine 2 HCl at a concentration of 0.021979 grams per liter;
(14) L-Glutamic Acid at a concentration of 0.012124 grams per liter;
(15) L-Glutamine at a concentration of 0.054292 grams per liter;
(16) Glycine at a concentration of 0.009904 grams per liter;
(17) L-Histidine HCl $H_2O$ at a concentration of 0.032817 grams per liter;
(18) Hydroxy-L-Proline at a concentration of 0.007629 grams per liter;
(19) L-Isoleucine at a concentration of 0.034649 grams per liter;
(20) L-Leucine at a concentration of 0.035609 grams per liter;
(21) L-Lysine HCl at a concentration of 0.053620 grams per liter;
(22) L-Methionine at a concentration of 0.009689 grams per liter;
(23) L-Ornithine HCl at a concentration of 0.003764 grams per liter;
(24) L-Phenylalanine at a concentration of 0.023494 grams per liter;
(25) L-Proline at a concentration of 0.009352 grams per liter;
(26) L-Serine at a concentration of 0.010600 grams per liter;
(27) L-Threonine at a concentration of 0.032895 grams per liter;
(28) L-Tryptophan at a concentration of 0.012276 grams per liter;
(29) L-Tyrosine 2 Na $2H_2O$ at a concentration of 0.036860 grams per liter;
(30) L-Valine at a concentration of 0.034268 grams per liter;
(31) Adenine sulfate at a concentration of 0.005993 grams per liter;
(32) Adenosine at a concentration of 0.003007 grams per liter;
(33) L-Ascorbic Acid Na at a concentration of 0.020030 grams per liter;
(34) D-Biotin at a concentration of 0.000016 grams per liter;
(35) Calciferol at a concentration of 0.000158 grams per liter;
(36) Choline Chloride at a concentration of 0.001028 grams per liter;
(37) Folic Acid at a concentration of 0.000538 grams per liter;
(38) I-Inositol at a concentration of 0.001055 grams per liter;
(39) Inosine at a concentration of 0.005993 grams per liter;
(40) Myo-Inositol at a concentration of 0.000050 grams per liter;
(41) Menadione (Sodium Bisulfite) at a concentration of 0.000016 grams per liter;
(42) Niacin at a concentration of 0.000015 grams per liter;
(43) Niacinamide at a concentration of 0.000553 grams per liter;
(44) Nicotinic Acid at a concentration of 0.000025 grams per liter;
(45) P-Amino Benzoic Acid at a concentration of 0.000080 grams per liter;
(46) D-Ca Pantothenate at a concentration of 0.000528 grams per liter;
(47) D-Panthothenic Acid (Hemicalcium) at a concentration of 0.000010 grams per liter;
(48) Pyridoxal HCl at a concentration of 0.000553 grams per liter;
(49) Pyridoxine HCl at a concentration of 0.000175 grams per liter;
(50) Retinol Acetate at a concentration of 0.000100 grams per liter;
(51) Riboflavin at a concentration of 0.000063 grams per liter;
(52) Thiamine HCl at a concentration of 0.000538 grams per liter;
(53) DL-α-Tocopherol Phosphate 2 Na at a concentration of 0.000016 grams per liter;
(54) Vitamin B-12 at a concentration of 0.004818 grams per liter;
(55) L-Amino-n-Butyric Acid at a concentration of 0.002204 grams per liter;
(56) Cocarboxylase at a concentration of 0.000400 grams per liter;
(57) Coenzyme A Na at a concentration of 0.001000 grams per liter;
(58) 2'-Deoxyadenosine at a concentration of 0.004000 grams per liter;
(59) 2'-Deoxycytidine HCl at a concentration of 0.004000 grams per liter;
(60) 2'-Deoxyguanosine at a concentration of 0.004000 grams per liter;
(61) Flavin Adenine Dinucleotide 2 Na at a concentration of 0.000400 grams per liter;
(62) D-Glucosamine HCl at a concentration of 0.001540 grams per liter;
(63) D-Glucose at a concentration of 0.927557 grams per liter;
(64) Glucuronate Na at a concentration of 0.000720 grams per liter;

(65) D-Glucuronolactone at a concentration of 0.000720 grams per liter;
(66) Glutathione Na at a concentration of 0.008000 grams per liter;
(67) 5' Methylcytosine HCl at a concentration of 0.000040 grams per liter;
(68) B-NAD at a concentration of 0.002800 grams per liter;
(69) B-NADP Na at a concentration of 0.000400 grams per liter;
(70) Phenol Red Na at a concentration of 0.013276 grams per liter;
(71) Taurine at a concentration of 0.001672 grams per liter;
(72) Thymidine at a concentration of 0.004000 grams per liter;
(73) Tween 80 at a concentration of 0.005000 grams per liter;
(74) Uridine 5'-Triphosphate Na at a concentration of 0.000400 grams per liter;
(75) HEPES at a concentration of 3.143182 grams per liter;
(76) Cholesterol at a concentration of 0.000120 grams per liter;
(77) Sodium Bicarbonate at a concentration of 2.320000 grams per liter;
(78) Sodium Pyruvate at a concentration of 0.0660000 grams per liter;
(79) Gentamycin at a concentration of 0.0900000 grams per liter;
(80) Streptomycin at a concentration of 0.1200000 grams per liter;
(81) 2-Mercaptoethanol at a concentration of 0.3 mM;
(82) Chondroitin Sulfate at a concentration of 3.000000 grams per liter;
(83) L-Ascorbic Acid at a concentration of 0.010566 grams per liter;
(84) L-Alynyl-L-Glutamine at a concentration of 2 mM;
(85) Glutathione Na Reduced at a concentration of 0.307000 grams per liter;
(86) (+)-α-Tocopherol Acetate at a concentration of 0.441120 grams per liter;
(87) Recombinant human insulin at a concentration of 0.006000 grams per liter;
(88) Recombinant human PDGF-BB at a concentration of 0.000200 grams per liter;
(89) B-estradiol at a concentration of 0.000001 grams per liter;
(90) Progesterone at a concentration of 0.000002 grams per liter;
(91) D-Carnitine HCl at a concentration of 0.002500 grams per liter;
(92) Pyridoxal-5-Phosphate at a concentration of 0.001000 grams per liter;
(93) Betaine HCl at a concentration of 0.001250 grams per liter;
(94) L-α-Phosphatidyl Choline at a concentration of 0.000500 grams per liter;
(95) Hypoxanthine at a concentration of 0.000180 grams per liter;
(96) 2-Deoxy-D-Ribose at a concentration of 0.000300 grams per liter;
(97) D-Ribose at a concentration of 0.000300 grams per liter;
(98) Xanthine at a concentration of 0.000206 grams per liter;
(99) $CuSO_4.5H_2O$ at a concentration of $1.60 \times 10^{-06}$ grams per liter;
(100) $ZnSO_4.7H_2O$ at a concentration of $8.63 \times 10^{-04}$ grams per liter;
(101) Selenite Na at a concentration of $1.73 \times 10^{-05}$ grams per liter;
(102) Ferric Citrate at a concentration of $1.16 \times 10^{-03}$ grams per liter;
(103) $MnSO_4.H_2O$ at a concentration of $1.70 \times 10^{-08}$ grams per liter;
(104) $NaSiO_3.9H_2O$ at a concentration of $1.40 \times 10^{-05}$ grams per liter;
(105) Molybdic Acid, Ammonium Salt at a concentration of $1.24 \times 10^{-07}$ grams per liter;
(106) $NH_4VO_3$ at a concentration of $6.50 \times 10^{-08}$ grams per liter;
(107) $NiSO_4.6H_2O$ at a concentration of $1.30 \times 10^{-08}$ grams per liter;
(108) $SnCl_2$ (anhydrous) at a concentration of $1.20 \times 10^{-08}$ grams per liter;
(109) $AlCl_3.6H_2O$ at a concentration of $1.20 \times 10^{-07}$ grams per liter;
(110) $AgNO_3$ at a concentration of $1.70 \times 10^{-08}$ grams per liter;
(111) $Ba(C_2H_3O_2)_2$ at a concentration of $2.55 \times 10^{-07}$ grams per liter;
(112) KBr at a concentration of $1.20 \times 10^{-08}$ grams per liter;
(113) $CdCl_2$ at a concentration of $2.28 \times 10^{-07}$ grams per liter;
(114) $CoCl_2$ at a concentration of $2.38 \times 10^{-07}$ grams per liter;
(115) $CrCl_3$ (anhydrous) at a concentration of $3.20 \times 10^{-08}$ grams per liter;
(116) NaF at a concentration of $4.20 \times 10^{-07}$ grams per liter;
(117) $GeO_2$ at a concentration of $5.30 \times 10^{-08}$ grams per liter;
(118) KI at a concentration of $1.70 \times 10^{-08}$ grams per liter;
(119) RbCl at a concentration of $1.21 \times 10^{-07}$ grams per liter; and,
(120) $ZrOCl_2.8H_2O$ at a concentration of $3.22 \times 10^{-07}$ grams per liter.

33. The method of claim 31, wherein the method is part of a method of keratoplasty comprising the steps of:
   a. providing an excised cornea;
   b. providing a serumfree medium for in vitro storage of cornea tissue, the serumfree medium characterized by an ability to maintain cornea viability during in vitro storage for 28 days at a temperature from about 31° C. to about 37° C. with only a single medium replacement at 14 days of in vitro storage; and,
   c. storing the excised cornea in the serumfree medium.

34. The method of keratoplasty of claim 33, wherein the serumfree solution consists of:
   (1) Calcium Chloride $2H_2O$ at a concentration 0.106000 grams per liter;
   (2) Calcium Chloride (anhydrous) at a concentration of 0.105511 grams per liter;

(3) Magnesium Sulfate (anhydrous) at a concentration of 0.091526 grams per liter;
(4) Potassium Chloride at a concentration of 0.371023 grams per liter;
(5) Sodium Acetate (anhydrous) at a concentration of 0.012000 grams per liter;
(6) Sodium Chloride at a concentration of 6.069984 grams per liter;
(7) Sodium Phosphate Monobasic (anhydrous) at a concentration of 0.122658 grams per liter;
(8) Ferric Nitrate at a concentration of 0.000301 grams per liter;
(9) L-Alanine at a concentration of 0.017932 grams per liter;
(10) L-Arginine HCl at a concentration of 0.078936 grams per liter;
(11) L-Asparagine $H_2O$ at a concentration of 0.012676 grams per liter;
(12) L-Aspartic Acid at a concentration of 0.011944 grams per liter;
(13) L-Cystine 2 HCl at a concentration of 0.021979 grams per liter;
(14) L-Glutamic Acid at a concentration of 0.012124 grams per liter;
(15) L-Glutamine at a concentration of 0.054292 grams per liter;
(16) Glycine at a concentration of 0.009904 grams per liter;
(17) L-Histidine HCl $H_2O$ at a concentration of 0.032817 grams per liter;
(18) Hydroxy-L-Proline at a concentration of 0.007629 grams per liter;
(19) L-Isoleucine at a concentration of 0.034649 grams per liter;
(20) L-Leucine at a concentration of 0.035609 grams per liter;
(21) L-Lysine HCl at a concentration of 0.053620 grams per liter;
(22) L-Methionine at a concentration of 0.009689 grams per liter;
(23) L-Ornithine HCl at a concentration of 0.003764 grams per liter;
(24) L-Phenylalanine at a concentration of 0.023494 grams per liter;
(25) L-Proline at a concentration of 0.009352 grams per liter;
(26) L-Serine at a concentration of 0.010600 grams per liter;
(27) L-Threonine at a concentration of 0.032895 grams per liter;
(28) L-Tryptophan at a concentration of 0.012276 grams per liter;
(29) L-Tyrosine 2 Na $2H_2O$ at a concentration of 0.036860 grams per liter;
(30) L-Valine at a concentration of 0.034268 grams per liter;
(31) Adenine sulfate at a concentration of 0.005993 grams per liter;
(32) Adenosine at a concentration of 0.003007 grams per liter;
(33) L-Ascorbic Acid Na at a concentration of 0.020030 grams per liter;
(34) D-Biotin at a concentration of 0.000016 grams per liter;
(35) Calciferol at a concentration of 0.000158 grams per liter;
(36) Choline Chloride at a concentration of 0.001028 grams per liter;
(37) Folic Acid at a concentration of 0.000538 grams per liter;
(38) I-Inositol at a concentration of 0.001055 grams per liter;
(39) Inosine at a concentration of 0.005993 grams per liter;
(40) Myo-Inositol at a concentration of 0.000050 grams per liter;
(41) Menadione (Sodium Bisulfite) at a concentration of 0.000016 grams per liter;
(42) Niacin at a concentration of 0.000015 grams per liter;
(43) Niacinamide at a concentration of 0.000553 grams per liter;
(44) Nicotinic Acid at a concentration of 0.000025 grams per liter;
(45) P-Amino Benzoic Acid at a concentration of 0.000080 grams per liter;
(46) D-Ca Pantothenate at a concentration of 0.000528 grams per liter;
(47) D-Panthothenic Acid (Hemicalcium) at a concentration of 0.000010 grams per liter;
(48) Pyridoxal HCl at a concentration of 0.000553 grams per liter;
(49) Pyridoxine HCl at a concentration of 0.000175 grams per liter;
(50) Retinol Acetate at a concentration of 0.000100 grams per liter;
(51) Riboflavin at a concentration of 0.000063 grams per liter;
(52) Thiamine HCl at a concentration of 0.000538 grams per liter;
(53) DL-α-Tocopherol Phosphate 2 Na at a concentration of 0.000016 grams per liter;
(54) Vitamin B-12 at a concentration of 0.004818 grams per liter;
(55) L-Amino-n-Butyric Acid at a concentration of 0.002204 grams per liter;
(56) Cocarboxylase at a concentration of 0.000400 grams per liter;
(57) Coenzyme A Na at a concentration of 0.001000 grams per liter;
(58) 2'-Deoxyadenosine at a concentration of 0.004000 grams per liter;
(59) 2'-Deoxycytidine HCl at a concentration of 0.004000 grams per liter;
(60) 2'-Deoxyguanosine at a concentration of 0.004000 grams per liter;
(61) Flavin Adenine Dinucleotide 2 Na at a concentration of 0.000400 grams per liter;
(62) D-Glucosamine HCl at a concentration of 0.001540 grams per liter;
(63) D-Glucose at a concentration of 0.927557 grams per liter;
(64) Glucuronate Na at a concentration of 0.000720 grams per liter;

(65) D-Glucuronolactone at a concentration of 0.000720 grams per liter;
(66) Glutathione Na at a concentration of 0.008000 grams per liter;
(67) 5' Methylcytosine HCl at a concentration of 0.000040 grams per liter;
(68) B-NAD at a concentration of 0.002800 grams per liter;
(69) B-NADP Na at a concentration of 0.000400 grams per liter;
(70) Phenol Red Na at a concentration of 0.013276 grams per liter;
(71) Taurine at a concentration of 0.001672 grams per liter;
(72) Thymidine at a concentration of 0.004000 grams per liter;
(73) Tween 80 at a concentration of 0.005000 grams per liter;
(74) Uridine 5'-Triphosphate Na at a concentration of 0.000400 grams per liter;
(75) HEPES at a concentration of 3.143182 grams per liter;
(76) Cholesterol at a concentration of 0.000120 grams per liter;
(77) Sodium Bicarbonate at a concentration of 2.320000 grams per liter;
(78) Sodium Pyruvate at a concentration of 0.0660000 grams per liter;
(79) Gentamycin at a concentration of 0.0900000 grams per liter;
(80) Streptomycin at a concentration of 0.1200000 grams per liter;
(81) 2-Mercaptoethanol at a concentration of 0.3 mM;
(82) Chondroitin Sulfate at a concentration of 3.000000 grams per liter;
(83) L-Ascorbic Acid at a concentration of 0.010566 grams per liter;
(84) L-Alynyl-L-Glutamine at a concentration of 2 mM;
(85) Glutathione Na Reduced at a concentration of 0.307000 grams per liter;
(86) (+)-α-Tocopherol Acetate at a concentration of 0.441120 grams per liter;
(87) Recombinant human insulin at a concentration of 0.006000 grams per liter;
(88) Recombinant human PDGF-BB at a concentration of 0.000200 grams per liter;
(89) B-estradiol at a concentration of 0.000001 grams per liter;
(90) Progesterone at a concentration of 0.000002 grams per liter;
(91) D-Carnitine HCl at a concentration of 0.002500 grams per liter;
(92) Pyridoxal-5-Phosphate at a concentration of 0.001000 grams per liter;
(93) Betaine HCl at a concentration of 0.001250 grams per liter;
(94) L-α-Phosphatidyl Choline at a concentration of 0.000500 grams per liter;
(95) Hypoxanthine at a concentration of 0.000180 grams per liter;
(96) 2-Deoxy-D-Ribose at a concentration of 0.000300 grams per liter;
(97) D-Ribose at a concentration of 0.000300 grams per liter;
(98) Xanthine at a concentration of 0.000206 grams per liter;
(99) $CuSO_4.5H_2O$ at a concentration of $1.60 \times 10^{-06}$ grams per liter;
(100) $ZnSO_4.7H_2O$ at a concentration of $8.63 \times 10^{-04}$ grams per liter;
(101) Selenite Na at a concentration of $1.73 \times 10^{-05}$ grams per liter;
(102) Ferric Citrate at a concentration of $1.16 \times 10^{-03}$ grams per liter;
(103) $MnSO_4.H_2O$ at a concentration of $1.70 \times 10^{-08}$ grams per liter;
(104) $NaSiO_3.9H_2O$ at a concentration of $1.40 \times 10^{-05}$ grams per liter;
(105) Molybdic Acid, Ammonium Salt at a concentration of $1.24 \times 10^{-07}$ grams per liter;
(106) $NH_4VO_3$ at a concentration of $6.50 \times 10^{-08}$ grams per liter;
(107) $NiSO_4.6H_2O$ at a concentration of $1.30 \times 10^{-08}$ grams per liter;
(108) $SnCl_2$ (anhydrous) at a concentration of $1.20 \times 10^{-08}$ grams per liter;
(109) $AlCl_3.6H_2O$ at a concentration of $1.20 \times 10^{-07}$ grams per liter;
(110) $AgNO_3$ at a concentration of $1.70 \times 10^{-08}$ grams per liter;
(111) $Ba(C_2H_3O_2)_2$ at a concentration of $2.55 \times 10^{-07}$ grams per liter;
(112) $KBr$ at a concentration of $1.20 \times 10^{-08}$ grams per liter;
(113) $CdCl_2$ at a concentration of $2.28 \times 10^{-07}$ grams per liter;
(114) $CoCl_2$ at a concentration of $2.38 \times 10^{-07}$ grams per liter;
(115) $CrCl_3$ (anhydrous) at a concentration of $3.20 \times 10^{-08}$ grams per liter;
(116) $NaF$ at a concentration of $4.20 \times 10^{-07}$ grams per liter;
(117) $GeO_2$ at a concentration of $5.30 \times 10^{-08}$ grams per liter;
(118) $Kl$ at a concentration of $1.70 \times 10^{-08}$ grams per liter;
(119) $RbCl$ at a concentration of $1.21 \times 10^{-07}$ grams per liter; and,
(120) $ZrOCl_2.8H_2O$ at a concentration of $3.22 \times 10^{-07}$ grams per liter.

35. The method of keratoplasty of claim 33, further comprising the step of:
  d. thinning the excised cornea, after in vitro storage, by contacting the excised cornea with a deturgescent solution.

36. The method of claim 35, wherein the deturgescent solution is selected from the group consisting of:
  a. Optisol; and,
  b. Optisol-GS.

37. The method of keratoplasty of claim 33, further comprising the step of implanting the excised cornea after in vitro storage in the serumfree medium.

38. The method of keratoplasty of claim 37, wherein the serumfree medium is at a temperature from about 31° C. to about 37° C. during the in vitro storage step.

39. The method of keratoplasty of claim 38, wherein the in vitro storage step lasts at least 14 days.

40. The method of keratoplasty of claim 38, wherein the in vitro storage step lasts in excess of 14 days and the serumfree medium is replaced at not more than 14 days from commencing in vitro storage.

41. The method of keratoplasty of claim 38, wherein the in vitro storage step lasts in excess of 14 days and the serumfree medium is replaced at not more than 14 days intervals.

* * * * *